United States Patent [19]
Demetriou et al.

[11] Patent Number: 5,866,329
[45] Date of Patent: Feb. 2, 1999

[54] METHOD AND PROBE FOR DETECTION OF GENE ASSOCIATED WITH LIVER NEOPLASTIC DISEASE

[76] Inventors: Achilles A. Demetriou, 11805 Gwynne La., Bel Air, Calif. 90077; Julia Y. Ljubimova, 7320 Hawthorne Ave., #308, Los Angeles, Calif. 90046

[21] Appl. No.: 533,996

[22] Filed: Sep. 27, 1995

[51] Int. Cl.$^6$ .............................. C12Q 1/68; C07H 21/00; C07H 21/02; C07H 21/04
[52] U.S. Cl. .......................... 435/6; 435/91.1; 435/252.3; 435/320.1; 536/24.31
[58] Field of Search ........................... 435/6, 91.1, 172.3, 435/320.1, 252.3; 514/44; 536/23.1, 23.5, 24.3, 24.31, 24.5; 935/8, 78, 66, 72

[56] References Cited

U.S. PATENT DOCUMENTS

| | | | |
|---|---|---|---|
| 5,312,733 | 5/1994 | MacLeod | 435/69.1 |
| 5,342,761 | 8/1994 | MacLeod | 435/69.1 |
| 5,403,926 | 4/1995 | Yang et al. | 536/23.6 |

FOREIGN PATENT DOCUMENTS

| | | |
|---|---|---|
| 0 351 458 A | 1/1990 | European Pat. Off. . |
| 91/09045 | 6/1991 | WIPO . |
| 9109045 | 6/1991 | WIPO . |
| 9213097 | 8/1992 | WIPO . |
| WO 94 10199 A | 5/1994 | WIPO . |

OTHER PUBLICATIONS

Izuno, L. et al., "Early Detection of Hepatocellular Carcinoma Associated Wtih Cirrhosis By Combined Assay of Des-y-Carboxy Prothrombin and Alpha-Fetoprotein: A Prospective Study" *Hepato-Gastroenterology*, 42(4):387-393 (Jul. 1995).

Ljubimova, J. et al., "A Novel*abl*-Like Gene Associated With Liver Cirrhosis and HCC," *Hepatology*, 22(4):329 (Nov. 1995).

Bisgaard, H.C., et al., "Phenotypic Modulation of Keratins, Vimentin, And α-Fetoprotein In Cultured Rat Liver Epithelial Cells After Chemical, Oncogene, And Spontaneous Transformation." *J. Cell. Physiol.*, 159 (3):485-494 (1994).

Bois-Joyeux, B., et al., "The *c-jun*Proto-Oncogene Down-Regulates The Rat α-Fetoprotein Promoter in HepG2 Hepatoma Cells Without Binding To DNA." *J. Biol. Chem.*, 270 (17):10204-10211 (1995).

Chan, A.M-L., et al., "Expression cDNA Cloning Of A Novel Oncogene With Sequence Similarity To Regulators Of Small GTP-Binding Proteins." *Oncogene*, 9(4):1057-1063 (1994).

Carcillo, J.A., et al., "Oncogene Expression: A New Horizon In The Study Of Sepsis." *Prog. Clin. Biols. Res.*, 286 (Mol. Cell. Mech. Septic Shock):71-76 (1989).

Farshia, M., et al., "Expression of Oncogenes And Tumor Suppressor Genes In Human Hepatocellular Carcinoma And Hepatoblastoma Cell Lines." *J. Med. Virol.*, 38 (4):235-239 (1992).

Fox,T.R.,etal., "Detection Of A Cellular Oncogene In Spontaneous Liver Tumors Of B6C3F1 Mice." *Science*, 228 (4699):596-597 (1985).

Gu, J-R., et al. "Oncogenes In Human Primary Hepatic Cancer." *J. Cell. Physiol.*, Supplement 4:13-20 (1986).

Imaseki, H., et al., "Expression Of c-myc Oncogene In Colorectal Polyps As A Biological Marker For Monitoring Malignant Potential." *Cancer (Philadelphia)*, 64 (3):704-709 (1989).

Matsubara, K., et al., "A Novel Oncogene From A Human Hepatocellular Carcinoma." *Proc. Int. Symp. Princess Takamatsu Cancer Res. Fund*, 17 (Oncog. Cancer):133-141 (1987).

Oda, T., et al., "Mutation Pattern Of The p53 Gene As A Diagnostic Market For Multiple Hepatocellular Carcinoma." *Cancer Res.*, 52(13):3674-3678 (1992).

Pasquinelli, et al., "Multiple Oncognes And Tumor Suppressor Genes Are Structurally and Functionally Intact During Hepatocarcinogenesis In Hepatitis B Virus Transgenic Mice." *Cancer Res.*, 52(10):2823-2829 (1992).

Sandgren, E.P., et al., "Oncogen-Induced Liver Neoplasia In Transgenic Mice." *Oncogene*, 4 (6):715-724 (1989).

Shiozawa, M., et al., "The *1ca*as an Onco-Fetal Gene; Its Expression in Human Fetal Liver." *Oncogene*, 2 (5):523-526 (1988).

Stanley, L.A., "Proto-Oncogene Activation In Liver Tumors of Hepatocarcinogenesis-Resistant Strains of Mice." *Carcinogenesis (London)*, 13 (12):2427-2433 (1992).

Takagi, H., et al., "Molecular And Genetic Analysis Of Liver Oncognesis In Transforming Growth Factor αTransgenic Mice." *Cancer Res.*, 52 (19):5171-5177 (1992).

Van Beneden, R.J., "Oncogenes In Hematopoietic And Hepatic Fish Neoplasms." *Cancer Res.*, 50 (17, Supp.):5671s-5674s (1990).

*Primary Examiner*—George C. Elliott
*Assistant Examiner*—Thomas G. Larson

[57] ABSTRACT

The present invention provides a gene that encodes proteins associated with liver neoplastic diseases, such as liver cirrhosis and hepatocellular carcinoma. Significantly, these proteins are not expressed in normal, non-neoplastic liver. In accordance with the present invention there also are provided antibodies that are capable of binding to the invention proteins, as well as methods and kits for screening for liver neoplastic diseases.

55 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 154 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens
        ( F ) TISSUE TYPE: Liver ( i x ) FEATURE:
        ( A ) NAME/KEY: CDS
        ( B ) LOCATION: 24..154

( x i ) SEQUENCE DESCRIPTION: SEQ ID NO:1:

```
TGGTCCTTTG GCGTCGTCCT CAA GTT ATA TTA GAA TCG TGT CCT CCC AGC         50
                         Val Ile Leu Glu Ser Cys Pro Pro Ser
                          1               5

TTT GGC CAG CTT ACT ATT CTA GGA CTT GAT TCC TTC ATT CAG TCA CAA       98
Phe Gly Gln Leu Thr Ile Leu Gly Leu Asp Ser Phe Ile Gln Ser Gln
 10              15                  20                  25

TTT ATT GAG CAC CGA CTT TGC ATC AAG CTC TTG CTG AAG ATA ACG CTG      146
Phe Ile Glu His Arg Leu Cys Ile Lys Leu Leu Leu Lys Ile Thr Leu
                 30                  35                  40

ATG ATG AG                                                           154
Met Met
```

( 2 ) INFORMATION FOR SEQ ID NO:2:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val Ile Leu Glu Ser Cys Pro Pro Ser Phe Gly Gln Leu Thr Ile Leu
 1               5                  10                  15

Gly Leu Asp Ser Phe Ile Gln Ser Gln Phe Ile Glu His Arg Leu Cys
             20                  25                  30

Ile Lys Leu Leu Leu Lys Ile Thr Leu Met Met
             35                  40
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:3:

```
TGGTCCTTTG GCGTCGTCCT C                                               21
```

( 2 ) INFORMATION FOR SEQ ID NO:4:

-continued (i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (xi) SEQUENCE DESCRIPTION: SEQ ID NO:4:

CTCATCATCA GCGTTATCTT C                                      21

(2) INFORMATION FOR SEQ ID NO:5:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (xi) SEQUENCE DESCRIPTION: SEQ ID NO:5:

AAGTTATATT AGAATCGTGT C                                      21

(2) INFORMATION FOR SEQ ID NO:6:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (xi) SEQUENCE DESCRIPTION: SEQ ID NO:6:

CAAGAGCTTG ATGCAAAGTC G                                      21

METHOD AND PROBE FOR DETECTION OF GENE ASSOCIATED WITH LIVER NEOPLASTIC DISEASE

FIELD OF THE INVENTION

The present invention relates to a gene that encodes protein associated with liver neoplastic diseases, such as liver cirrhosis and hepatocellular carcinoma. The protein encoded by the gene of this invention is not expressed in normal, non-neoplastic liver tissue. The present invention also relates to methods and kits for screening for liver neoplastic disease.

BACKGROUND OF THE INVENTION

Hepatocellular carcinoma (HCC) is reported to afflict as many as 260,000 individuals each year world-wide, making it the eighth most frequent cancer in the world. Cirrhosis has been implicated as a predisposing condition for HCC in a majority of patients who develop HCC in low risk populations. Approximately eighty to ninety percent of HCC cases have been found to occur in patients suffering from cirrhotic liver. See, Lotze, M. T., et al., "Hepatobiliary Neoplasms," in *CANCER. Principles and Practice of Oncology*, Devita V. T. J. et al., eds., 883–915 (1993); Azzarone, F. A., et al., Eur. J. Cancer Prevention, 1 (Suppl. 3):55–58 (1992).

Current therapies for liver cirrhosis include treatment with corticosteroids and interferon-α. However, in more severe cases, a liver transplant is often the only recourse. Similarly, treatment for benign and malignant liver tumors is often either a liver resection or a liver transplant. These more drastic treatments are both very risky and very expensive. Thus, early diagnosis and treatment of liver neoplastic diseases, such as liver cirrhosis and HCC, is highly desirable.

It has been reported that α-fetoprotein and IGF-II are expressed in the liver tissue of approximately 30% of those individuals afflicted with HCC, but not in normal adult liver. Unfortunately, these proteins appear more frequently in late stage HCC and thus, are not suitable for the development of an early diagnostic test.

Efforts to develop methods for diagnosis and treatment have been slowed by the lack of understanding of the pathology of HCC. In spite of the clinical importance of liver cirrhosis and HCC, the mechanism of HCC development still remains obscure. Tremendous gaps exist in the current understanding of basic pathologic mechanisms that lead to the development of HCC. Accordingly, the identification of genetic markers associated with liver neoplastic diseases, such as liver cirrhosis and HCC, for use as a tool in diagnosis and in the further elucidation of the pathology of these diseases, is highly desirable.

BRIEF DESCRIPTION OF THE INVENTION

The present invention provides a gene that encodes proteins associated with liver neoplastic diseases, such as liver cirrhosis and hepatocellular carcinoma. Significantly, these proteins are not expressed in normal, non-neoplastic liver. The invention also provides antibodies that are capable of binding to the invention proteins, as well as methods and kits for screening for liver neoplastic disease. Accordingly, the invention is expected to have utility in the diagnosis and prevention of liver neoplastic disease.

DETAILED DESCRIPTION OF THE INVENTION

In accordance with the present invention there is provided DNA encoding peptides that are about 36 amino acids long and that are characteristically expressed in individuals afflicted with liver neoplastic diseases, such as cirrhosis and hepatocellular carcinoma (HCC), but not in individuals with normal, non-neoplastic liver function.

The terms "nucleic acid" and "polynucleic acid" refer herein to deoxyribonucleic acid and ribonucleic acid in all their forms, i.e., single and double-stranded DNA, cDNA, mRNA, and the like. As used herein, the term "encode" in its various grammatical forms includes nucleotides and/or amino acids which correspond to other nucleotides or amino acids in the transcriptional and/or translational sense.

The phrase "liver neoplastic disease" refers herein to diseases which are characterized by the development of abnormal tissue growth in the liver. Liver neoplastic diseases include, for example, liver cirrhosis, hepatocellular carcinoma, adenomatous hyperplasia, adenoma of the liver, and the like.

DNA contemplated in the practice of the present invention encodes a protein having the same, or substantially the same sequence as the amino acid sequence set forth in SEQ ID NO 2. As used herein, when the phrase "substantially the same" is used in conjunction with nucleic acid sequences, it refers to nucleic acid sequences having conservative substitutions (or non-consequential substitutions) as compared to the reference sequence. For example, substitutions in nucleotide sequences that do not substantially alter the function of the protein it encodes, or the tertiary structure of that protein, would be considered to produce a nucleic acid sequence that is substantially the same as the reference sequence.

When the phrase "substantially the same" is used in conjunction with amino acid sequences, it refers to amino acid sequences that result from substitutions that do not substantially alter the function of the protein or its tertiary structure. For example, substitution of a charged amino acid residue for a similarly charged amino acid residue or substitution of a non-polar amino acid residue for another non-polar amino acid residue would typically be considered to produce an amino acid sequence that is substantially the same as the reference sequence.

Set forth in SEQ ID NO 1 is an example of a DNA sequence that encodes a protein associated with liver neoplastic diseases, such as cirrhosis and hepatocellular carcinoma, but not normal, non-neoplastic liver. The sequence is 154 base pairs ("bp") in length and contains an open reading frame that extends from bp 24 to bp 132 of SEQ ID NO 1. Sequence searches conducted in GenBank indicate that the polynucleic acid sequence set forth in SEQ ID NO 1 is a novel gene. Set forth in SEQ ID NO 2 is the deduced amino acid sequence encoded by SEQ ID NO 1. A detailed description of the experimental methods used to discover the association between the expression of the polynucleic acid sequence set forth in SEQ ID NO 1 and liver neoplastic disease is provided in the "Examples" as set forth below.

The invention further relates to nucleotide probes that are sufficiently complementary to the above-described DNA to hybridize thereto, preferably under high stringency conditions. Exemplary probes include oligomers that are at least about 40 nucleic acid residues long and that are selected from any 40 or more contiguous residues of DNA of the present invention. Preferably, oligomeric probes used in the practice of the present invention are at least about 60 nucleic acid residues long. The present invention also contemplates oligomeric probes that are 150 nucleic acid residues long or longer. Those of ordinary skill in the art realize that nucleic acid probe technology is well known and that suitable hybridization conditions for achieving the hybridization of a probe of a particular length to polynucleotides of the present invention can readily be determined. Such manipulations to achieve optimizal hybridization conditions for probes of varying lengths are well known in the art. See, e.g., Sambrook et al., *Molecular Cloning: A Laboratory Manual*, Second Edition, Cold Spring Harbor (1989), incorporated herein by reference.

Preferably, oligomeric probes of the present invention are labelled to render them readily detectable. Detectable labels may be any species or moiety which may be detected either visually or with the aid of an instrument. Commonly used detectable labels are radioactive labels such as, for example, $^{32}P$, $^{14}C$, $^{125}I$, $^{3}H$, $^{35}S$, and the like. Biotin labeled nucleotides can be incorporated into DNA or RNA by such techniques as nick translation, chemical and enzymatic means, and the like. The biotinylated probes are detected after hybridization using indicating means such as avidin/streptavidin, fluorescent labeling agents, enzymes, colloidal gold conjugates, and the like. Nucleic acids may also be labeled with other fluorescent compounds, with immunodetectable fluorescent derivatives, with biotin analogues, and the like. Nucleic acids may also be labeled by means of attachment to a protein. Nucleic acids cross-linked to radioactive or fluorescent histone single-stranded binding protein may also be used. Those of ordinary skill in the art can recognize that there are other suitable methods for detecting oligomeric probes and other suitable detectable labels that are available for use in the practice of the present invention.

In another embodiment, the present invention relates to constructs that include the DNA described above, an origin of replication, and a promoter. The constructs of the invention are useful to introduce polynucleic acid sequences of the present invention into cells for either expression or replication. Selection and use of such constructs are well known to those of ordinary skill in the art and will vary in accordance with the cell targeted to receive the polynucleic acid. See, e.g., Sambrook et al., *Molecular Cloning: A Laboratory Manual*, Second Edition, Cold Spring Harbor (1989).

Introduction of the above-described constructs into appropriate host cells enables expression of the cloned polynucleic acid sequence. Appropriate expression vehicles are well known to those of ordinary skill in the art and include those that are replicable in eukaryotic cells and/or prokaryotic cells and those that remain episomal or those which integrate into the host cell genome. See, e.g., Sambrook et al., *Molecular Cloning: A Laboratory Manual*, Second Edition, Cold Spring Harbor (1989). Presently preferred vehicles for expression of the invention gene sequences in eukaryotic host cells, particularly mammalian cells, include Rexp (with an RSV LTR, Moloney murine leukemia virus LTR driven expression vector), and the like.

As used herein, a promoter region refers to a segment of polynucleic acid that controls transcription of DNA to which it is operatively linked. The promoter region includes specific sequences that are sufficient for RNA polymerase recognition, as well as binding and transcription initiation. This portion of the promoter region is referred to as the promoter. In addition, the promoter region includes sequences that modulate the recognition, binding and transcription initiation activity of RNA polymerase. Promoters, depending upon the nature of the regulation, may be constitutive or regulated. For example, promoters contemplated for use in the practice of the present invention include the SV40 early promoter, the cytomegalovirus (CMV) promoter, Moloney murine leukemia virus (MMLV) promoter, thymidine kinase promoter, albumin promoter, Rous Sarcoma virus promoter (RSV), and the like.

As used herein, the term "operatively linked" refers to the functional relationship of polynucleic acid sequences with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

In accordance with another embodiment of the present invention, there are provided host cells containing the above-described construct. Such host cells as bacterial, yeast and mammalian cells can be used for replicating polynucleic acids of the present invention and producing the same, or substantially the same polypeptide as set forth in SEQ ID NO. 2 under suitable expression conditions. Methods and conditions suitable to promote expression are well known in the art (see, e.g., Sambrook et al. *Molecular Cloning: A Laboratory Manual*, Second Edition, Cold Spring Harbor (1989)). Heterologous DNA may be introduced into host cells by any method known to those of skill in the art, such as for example, transfection with a vector encoding the heterologous DNA by $CaPO_4$ precipitation. See, e.g., Kashanchi, F., et al. *Nucleic Acids Research*, 20:4673–4674 (1992).

In yet another embodiment of the present invention, there are provided proteins that are about 36 amino acids long and that are characteristically expressed in individuals afflicted with liver neoplastic diseases, such as cirrhosis and HCC, but not in individuals with normal, non-neoplastic liver function. Suitable proteins include those having the same, or substantially the same sequence as the protein set forth in SEQ ID NO 2. As used herein, the terms "protein", "peptide" and "polypeptide" are considered to be equivalent terms and are used interchangeably.

The invention further includes antibodies that are capable of binding to the same, or substantially the same protein as set forth in SEQ ID NO 2. Such antibodies are expected to have utility in the diagnosis, prevention and treatment of liver neoplastic diseases. In this context, the term "antibody" encompasses monoclonal antibodies, polyclonal antibodies and humanized antibodies. For example, preferably for therapeutic applications, the antibodies employed will be humanized.

The above-described antibodies can be prepared employing standard techniques, as are well known to those of skill in the art, using the same, or substantially the same protein as set forth in SEQ ID NO 2, or fragments thereof, as antigens for antibody production. Polyclonal antibodies of the present invention are typically produced by immunizing a mammal with an inoculum containing the same, or substantially the same protein as set forth in SEQ ID NO 2, or fragments thereof, thereby inducing in the mammal, antibody molecules having immunospecificity for the protein set forth in SEQ ID NO 2, or fragments thereof.

To enhance the specificity of the antibody, the antibodies can be purified, for example, by immunoaffinity chromatography using solid phase-affixed immunizing polypeptide. Thus, purification is achieved by contacting antibody with the solid phase-affixed immunizing polypeptide for a time sufficient for the polypeptide to immunoreact with antibody to form a solid phase-affixed immunocomplex. Bound antibodies are then separated from the complex by standard techniques.

Monoclonal antibody production typically proceeds by isolating lymphocytes and fusing them with myeloma cells, thus producing hybridomas. The cloned hybridomas are then screened for production of antibodies specific for the same, or substantially the same protein as set forth in SEQ ID NO 2.

The antibody so produced can be used in diagnostic and assay methods to detect the presence or absence of protein associated with liver neoplastic disease. Thus, in accordance with another aspect of the invention are provided methods of screening for susceptibility to liver neoplastic disease. Such methods comprise:

a) contacting a sample with an invention antibody under conditions such that a complex of the antibody bound to protein associated with liver neoplastic disease is formed; and b) detecting the presence of the resulting complex.

The presence of a complex is indicative of susceptibility to liver neoplastic disease. Suitable "samples" include tissues, such as any liver tissue, or cells, such as a hepatocytes, and the like.

Preferably, antibodies of the present invention are detectably labelled to facilitate the identification of the presence of antibody-protein complex. Antibodies can be labelled with a variety of detectable compounds. For example, the detectable label can be a fluorescent labeling agent that chemically binds to antibodies without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamino-1-naphthalenesulfonyl chloride (DANSC), tetramethylrhodamine isothiocyanate (TRITC), lissamine, rhodamine 8200 sulphonyl chloride, and the like. A description of immunofluorescence analysis techniques is found in DeLuca, "Immunofluorescence Analysis", in *Antibody as a Tool*, Marchalonis et al., eds., John Wiley & Sons, Ltd., pp. 189–231 (1982), which is incorporated herein by reference.

Radioactive elements are also useful detectable labels. An exemplary radiolabeling agent is a radioactive element that produces gamma ray emissions. Elements which themselves emit gamma rays, such as $^{125}$I and $^{131}$I, represent one suitable class of gamma ray emission-producing radioactive element indicating groups.

In one embodiment, the detectable label is an enzyme, such as horseradish peroxidase (HRP), glucose oxidase, and the like. In such cases where the detectable marker is an enzyme (such as HRP or glucose oxidase), additional reagents are typically required to indicate that the antibody-protein complex has formed. Such additional reagents for HRP include hydrogen peroxide and an oxidation dye precursor such as diaminobenzidine, o-phenylenediamine dihydrochloride and the like. An additional reagent useful with glucose oxidase is 2,2'-azino-di-(3-ethyl-benzthiazoline-G-sulfonic acid).

Depending on the nature of the label or catalytic signal producing system used, a signal can be detected by irradiating the complexed test sample with light and observing the level of fluorescence; by contacting the complexed sample with a substrate which can be catalytically converted by the label to produced a dye, fluorescence or chemiluminescence, in which the formation of dye can be observed visually or in a spectrophotometer; or, in the case of chemiluminescence or a radioactive label, by employing a radiation counter such as a gamma counter or gamma emitting labels such as $^{125}$I. For detection of enzyme-catalyzed labels when the presently preferred combination of HRP is used as the enzyme and o-phenylenediamine dihydrochloride as the substrate, a quantitative analysis of complex can be made using a spectrophotometer (for example a EMAX Microplate Reader; available from Molecular Devices, Menlo Park, Calif.) at 405 nm in accordance with the manufacturer's instructions.

One method for detecting the presence of antibody-bound complex employs an "ELISA" format that provides for the detection and quantification of either antibody or antigen (depending on the ELISA format type) present in a sample. ELISA format is a well-known technique that can be readily carried out by those of ordinary skill in the art. A description of the ELISA technique is found in Chapter 22 of the 4th Edition of *Basic and Clinical Immunology*, by D. P. Sites et al., published by Lange Medical Publications of Los Altos, Calif. in 1982, incorporated herein by reference.

Useful solid matrices are also well known in the art. Such materials are water insoluble and include cross-linked dextran (available from Pharmacia Fine Chemicals; Piscataway, N.J.); agarose; polystyrene beads (typically about 1 micron to about 5 millimeters in diameter; available from Abbott Laboratories; North Chicago, Ill.); polyvinyl chloride; polystyrene; cross-linked polyacrylamide; nitrocellulose- or nylon-based webs such as sheets, strips or paddles; or tubes, plates or the wells of a microtiter plate, such as those made from polystyrene or polyvinylchloride; and the like.

In accordance with another embodiment of the present invention there are provided antisense oligonucleotides and DNA sequences encoding antisense oligonucleotides. As contemplated in the practice of the present invention, antisense oligonucleotides and DNA sequences encoding antisense oligonucleotides can be readily prepared that can bind to and therefore block the synthesis of the RNA encoding the protein of the present invention. Thus, these compounds can be administered to patients to inhibit the development of liver neoplastic diseases, such as liver cirrhosis and HCC. One of ordinary skill in the art will appreciate that when compositions (e.g., antibodies, antisense oligonucleotides, or DNA sequences encoding antisense oligonucleotides) of the present invention are administered as therapeutic agents, it may be necessary to combine these compositions with other suitable components to form a suitable pharmaceutical composition. The particular composition will depend on the intended use and mode of administration.

The present invention contemplates pharmaceutical compositions useful for practicing the therapeutic methods described herein. Pharmaceutical compositions of the present invention may contain a physiologically acceptable carrier together with antisense oligonucleotides, DNA encoding antisense oligonucleotides, or antibodies, as described herein, dissolved or dispersed therein as an active ingredient. In a preferred embodiment, the pharmaceutical composition is not immunogenic when administered to a mammal or human patient for therapeutic purposes. This may be accomplished, for example, by commonly known techniques of "humanizing" antibodies wherein the constant regions of an antibody derived from a non-human animal is replaced with constant regions from a human.

As used herein, the term "pharmaceutically acceptable" and grammatical variations thereof, as they refer to compositions, carriers, diluents and reagents, are used to represent that the materials are capable of administration to a mammal without the production of undesirable physiological effects such as nausea, dizziness, gastric upset, and the like.

The preparation of a pharmaceutical composition that contains active ingredients dissolved or dispersed therein is well known in the art. Typically such compositions are prepared as injectables either as liquid solutions or suspensions; however, solid forms suitable for solution, or suspension in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol, and the like, as well as combinations of any two or more thereof.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like, as well as combinations of any two or more thereof.

Salts formed with the free carboxyl groups can also be derived from inorganic bases such as, for example, sodium hydroxide, ammonium hydroxide, potassium hydroxide, and the like; organic bases such as mono-, di-, and tri-alkyl and -aryl amines (e.g., triethylamine, diisopropyl amine, methyl amine, dimethyl amine, and the like); ethanolamines (e.g., ethanolamine, diethanolamine, and the like); and the like, as well as combinations of any two or more thereof.

Physiologically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to (or to the exclusion of) water. Exemplary of such additional liquid phases are glycerin, vegetable oils such as cottonseed oil, water-oil emulsions, and the like.

A therapeutically effective amount is a predetermined amount calculated to achieve the desired effect, i.e., inhibition of the development of liver neoplastic disease. The required dosage for inhibiting neoplastic disease will depend on a variety of factors, including age, weight, sex and medical condition of the patient, as well as the severity of the pathology, the route of administration, and the type of therapeutic agent used. A skilled physician or veterinarian can readily determine and prescribe the effective amount of the pharmaceutical composition required to treat the patient. Conventionally, one of ordinary skill in the art would employ relatively low doses initially and subsequently increase the dose until a maximum response is obtained.

Kits for use in screening for susceptibility for liver neoplastic disease are also provided by the present invention. Such kits can include all or some of the reagent primers, probes, antibodies and antisense oligonucleotides described herein for determining the presence or absence of the polynucleotides or proteins, described herein, that are associated with liver neoplastic disease.

Kits of the present invention may contain, for example, restriction endonuclease, one or more labeled cDNA probes, lyophilized antibody that is capable of binding to proteins of the present invention, lyophilized secondary antibodies that are conjugated to a fluorochrome or peroxidase (in combination with an appropriate amount of hydrogen peroxide substrate) and that are capable of binding antibodies that are reactive to proteins of the present invention, blocking solutions (e.g., normal goat or rabbit serum, 3% bovine serum albumin solution in physiological saline, and the like), or buffers (e.g., Tris-HCl, phosphate, EDTA, and the like).

The invention will now be described in greater detail by reference to the following non-limiting examples.

EXAMPLE 1

Characterization and Preparation of Liver Tissue Samples

Human liver tissue samples were obtained from the Department of Pathology at Cedars-Sinai Medical Center in Los Angeles, Calif. The study group included 28 men and 8 women, ranging in age from 4 years to 76 years of age (mean age 47.6 years). None of these individuals had distant metastasis or had been previously treated for HCC. All of the individuals had undergone liver biopsy and/or surgery within two years prior to the study. The tissue specimens were taken from the liver biopsy samples. All specimens were fixed in neutral buffered formalin and embedded in paraffin blocks, according to the method described by Greet, C. E., et al., "PCR Amplification from Paraffin-Embedded Tissues," *Anatomic Pathology,* 95:117–124 (1991).

Histological diagnosis of the tumors was verified by an experienced pathologist. The pathology results for this study group indicated the following: 1) 4 normal liver samples; 2) 9 samples positive for chronic liver disease caused by hepatitis C virus (HCV) (6 of these were also positive for liver cirrhosis and 3 were also positive for chronic active hepatitis (CAH)); and 3) 12 samples positive for alcoholic liver disease (ALD) (4 of these were also positive for HCV, 2 were also positive for liver adenoma, and 9 were also positive for HCC).

EXAMPLE 2

Extraction of mRNA from Liver Tissue

Messenger RNA was extracted from the liver biopsy samples of Example 1 using a modification of the acid guanidinium thiocyanate/phenol/chloroform method described by Chomczynski and Sacchi, *Anal. Biochem.,* 162:156–157 (1987). Specifically, crushed, frozen liver tissue biopsy samples from Example 1 were placed into test tubes. A 0.5 ml aliquot of a solution of 4M guanidine thiocyanate, 25 mM sodium citrate (pH 7.0), 0.5% N-lauroylsarcosine, and 0.1M 2-mercaptoethanol was added to the tissue sample in each test tube. The test tubes were agitated for up to 24 hours at room temperature. The following aliquots were added to each tube: 1) 0.1 ml of a chloroform/isoamyl alcohol 24:1 v/v solution.; 2) 0.5 ml of acid phenol; and 3) 50 $\mu$l of sodium acetate. The tubes were then centrifuged at a centrifugation rate of 12,000×G for 20 minutes to pellet the tissue. The aqueous phase from each tube was transferred by pipet into a clean tube. An aliquot of 1.5 ml of ethanol was added to the aqueous phase in each tube to precipitate the RNA. The tubes were allowed to stand on a test tube rack at −80° C. for 2 hours, then centrifuged again at a centrifugation rate of 12,000×G for 20 minutes to generate an RNA pellet.

The pellets were each washed with a 1 ml aliquot of 75% ethanol. After washing, the pellets were air-dried at room temperature for 5 minutes. The pellets were then resuspended in digestion buffer (10 mM Tris-HCl and 2 mM ethylenediamine tetraacetic acid (EDTA)), then treated with 20 units (U) of DNase-free RNase (Sigma Chemical Co., St. Louis, Mo.) for 30 minutes at 37° C. To remove the DNase-free RNase, the phenol/chloroform extraction procedure was repeated a second time on the pellet, immediately followed by ethanol precipitation, as described above. After the precipitation step, the pellets were washed in distilled water.

The optical density of RNA in distilled water was measured at wavelengths of 260 nm and 280 nm using a Beckman, DU 640 Spectrophotometer (U.S.A.). The $OD_{260}/OD_{280}$ ratio was used to quantitate the amount of RNA extracted and to determine the purity of each preparation.

EXAMPLE 3

Amplification of cDNA Generated by Reverse Transcription of mRNA

Reverse transcription of 1 mg of each mRNA sample from Example 2 and amplification of the resulting cDNA by polymerase chain reaction (PCR) was carried out using the GeneAmp® RNA PCR Kit (Perkin-Elmer-Cetus, Norwalk, Conn.) according to the manufacturer's directions.

For reverse transcription, oligo $d(T)_{16}$ (Perkin-Elmer-Cetus, Norwalk Conn.) was used to prime the synthesis of cDNA. For PCR amplification of the reverse transcribed cDNA, primers with the sequences identified as SEQ ID NO 3 ("upstream primer") and SEQ ID NO 4 ("downstream primer") were used. Two negative controls were used: 1) a sample containing water only; and 2) a sample devoid of RNA template, but otherwise containing all of the reverse transcription and PCR reagents. In addition, an RT-PCR positive control of RNA from pAW109, in 1 mM EDTA, 10 mM NaCl, 30 mg/ml E.Coli rRNA, and 10 mM Tris-HCL (pH 8) (all of which were provided in the GeneAmp® RNA PCR kit) was used.

The GeneAmp® PCR System 9600 (Perkin-Elmer-Cetus, Norwalk, Conn.) thermal cycler was used to control the PCR reactions. Programmable temperature cycling was performed with the following cycle profile: 94° C. for 1 minute, then 35 cycles of each of the following: 1) denaturation for 30 seconds at 94° C.; 2) annealing for 45 seconds at 55° C.; and 3) extension for 45 seconds at 72° C. After 35 cycles, the reaction tubes were incubated at 72° for 5 minutes, then cooled to 4° C. The amplified cDNA samples were characterized by electrophoresis on gels containing 3%:1% NuSieve:Seakemagarose (FMC, Rockland, Me.) at room temperature for 2 hours.

A search in the Genbank and EMBL nucleic acid sequence libraries using the Intelligenetics Suite (Intelligenetics, Inc., Mountain View, Calif.) program indicated that these primers would not hybridize to any other known nucleic acid sequences under the conditions used.

EXAMPLE 4

Sequencing of the Marker Gene

Sequencing of the marker gene was conducted according to the Sanger method of sequencing. Bands were cut from the gel used in Example 3 and sequenced using a Sequenase kit (United States Biochemical, Cleveland, Ohio) containing DNA polymerase (United States Biochemical, Cleveland, Ohio) and ($^{35}$S)dATP (Amersham, Arlington Heights, Ill.) according to the manufacturer's directions. Plasmid template CDNA was prepared for sequencing according to a commercial protocol provided by Promega Biotec (Madison, Wis.). The gels were photographed onto Kodak Diagnostic Film SB 100 (Rochester, N.Y.). An IBI Standard Sequencer, Model STS 45 (New Haven, Conn.) was used to sequence the gels.

A 154 base pair polynucleic acid was isolated and compared with known sequences in Genbank. No known gene matched this sequence. The sequence of this novel polynucleic acid is set forth as SEQ ID NO 1. The amino acid sequence predicted by this nucleic acid sequence is set forth in SEQ ID NO 2. Analysis of the predicted protein showed an open reading frame extending from bp 24 to bp 132 of the nucleic acid sequence set forth in SEQ ID NO 1.

EXAMPLE 5

Preparation of a cDNA Probe for Detecting Gene Product of the Polynucleotide

Primers were selected to isolate and amplify a cDNA probe complementary to cellular mRNA associated with the polynucleotide sequence set forth in SEQ ID NO 1. The primers identified as SEQ ID NO 5 ("upstream primer") and SEQ ID NO 6 ("downstream primer") were used in the polymerase chain reaction method described above in Example 3.

The isolated cDNA probe was characterized by electrophoresis on a 3%:1% NuSieve:Seakemagarose gel as described in Example 3, then sequenced according to the method described in Example 4. The amplified cDNA probe was 101 base pairs long and the sequence corresponded to a portion of the 154 base pair cDNA that was isolated in Example 3.

EXAMPLE 6

Screening of Normal and Diseased Liver Tissue by RT-PCR

Expression of the polynucleotide sequence identified in Example 4 was studied in 18 fresh-frozen liver biopsy samples by RT-PCR. Liver biopsy samples with the following pathologies were screened: 4 normal liver samples; 1 fulminant liver samples; 7 cirrhotic liver samples (2 with small HCC nodules), and 6 HCC liver samples. Messenger RNA was extracted from these samples as described in Example 2. RT-PCR was conducted to obtain amplified cDNA product using the methods described in Example 3. As in Example 5, primers used for PCR amplification are set forth in SEQ ID NO 5 ("upstream primer") and SEQ ID NO 6 ("downstream primer"). The cDNA obtained from each liver biopsy sample was characterized by electrophoresis on gels containing 3%:1% NuSieve:Seakemagarose (FMC, Rockland, Me.) at room temperature for 2 hours.

The results indicated that the normal and fulminant liver samples did not contain any cDNA associated with expression of the novel gene sequence set forth as SEQ ID NO 1. In contrast, cDNA associated with this novel gene sequence was detected in all of the cirrhotic liver samples, and 5 of the 6 HCC liver samples. These results confirmed that the novel gene is expressed in cirrhotic and HCC liver tissue, but not in normal liver tissue. Thus, this novel gene is a useful marker for screening for liver diseases such as cirrhosis and HCC.

EXAMPLE 7

Screening of Various Types of Tissue Samples for Expression of Novel Gene

Using the method described in Example 1, mRNA was extracted from tissue samples from the following human tissues: 2 placentas, 1 normal kidney, 1 breast carcinoma, 1 spleen from a patient with lymphocytic leukemia, 2 normal livers, and 2 livers with HCC. Complementary DNA was obtained from the mRNA by RT-PCR, as described in Example 3. The cDNA obtained from each tissue sample was characterized by electrophoresis on an agarose gel as described in Example 3.

Complementary DNA associated with the expression of the novel gene described in Example 4 was detected in tissue samples obtained from breast carcinoma, a spleen from a patient with lymphocytic leukemia, and the 2 liver tissue samples afflicted with HCC. In contrast, the cDNA associated with the novel gene was not detected in any of the tissue samples from normal, non-cancerous placenta, kidney and liver tissue. The absence of expression of the novel gene in normal tissue tested suggests that this gene may play an important role in the process of malignancy.

EXAMPLE 8

Method of Screening Tissue Samples for Expression of the Marker Gene by Northern Blot Analysis Messenger RNA is extracted from tissue samples as described in Example 2. The extracted mRNA is resolved on a 1.5% agarose-formaldehyde gel by applying 18 mAmps for 16 hours. The extracted mRNA is then transferred to a nylon membrane (Schleicher & Schull, Keene, N.H.) by capillary action. The transferred mRNA is fixed onto the membrane by exposing the mRNA and nylon membrane to short-wave ultraviolet radiation in a Stratalinker (Stratagene, La Jolla, Calif.) for 40 seconds according to the manufacturer's directions.

The membranes are pre-hybridized for 1 hour at 64° C. with a solution of 50% deionized formamide, 7% sodium dodecyl sulfate (SDS), 10% bovine serum albumin (Sigma, St. Louis, Mo.), 1 mM EDTA and 0.2M sodium phosphate (pH 7.2). The 101 bp cDNA probe for the novel gene, described in Example 5, is radiolabeled with $^{32}P$ by random primer oligolabeling in the presence of dCT ($\alpha^{32}P$). The nylon membranes are hybridized in the presence of the $^{32}P$-cDNA probes by adding the probes to the pre-hybridization solution for a hybridization period of 16 hours at 64° C. After hybridization, the membranes are briefly washed three times in a solution of 40 mM sodium phosphate, 1 mM EDTA, and 1% SDS at 64° C. for three short washes, followed by a final 1 hour wash. The membranes are exposed to pre-flashed Kodak XAR-5 film (Rochester, N.Y.) at −70° C. for 2 to 14 days.

A positive signal indicates the presence of marker gene-specific mRNA expressed in the respective tissue.

EXAMPLE 9

Preparation of Polyclonal Antibodies Raised against Marker Gene Product

Peptides synthesized according to the sequence set forth in SEQ ID NO 2 are conjugated to keyhole limpet hemocyanin (KLH) and bovine serum albumin (BSA) according to the manufacturer's instructions (Imgect, Immunogen Conjugation Kit from Pierce Chemical Co., Rockford, Ill.). Immunogen is prepared by mixing KLH-conjugated peptides thoroughly with Freund's complete adjuvant (Pierce Chemical Co., Rockford, Ill.) in a 1:1 v/v ratio. A dose of 100–200 µg of the immunogen is then injected subcutaneously in 10 sites in 3 young New Zealand White rabbits per peptide. Just prior to immunization, 5–10 ml of preimmune blood is collected through the ear vein. On days 14 and 28, the rabbits are boosted by the same injection route using immunogen in incomplete Freund's adjuvant. Starting from day 28, blood is collected twice a week (up to 30 ml each time) for up to 3 months and assayed by standard peroxidase/DAB-based ELISA (kit from Pierce) against BSA-conjugated peptide, with preimmune serum as a negative control. Sera from positive bleeds are pooled and IgG is isolated by protein A-agarose (Sigma, St. Louis, Mo.) affinity chromatography. Immune IgG is further purified by affinity chromatography on columns with peptide immobilized on agarose beads. Purified IgG is tested for reaction by immunoprecipitation, Western blotting and immunohistochemistry.

EXAMPLE 10

Preparation of Monoclonal Antibody having Binding Specificity to Novel Marker Gene Product Peptides synthesized according to the sequence set forth in SEQ ID NO 2 are conjugated to keyhole limpet hemocyanin (KLH) and bovine serum albumin (BSA) according to the manufacturer's instructions (Imgect, Immunogen Conjugation Kit from Pierce Chemical Co., Rockford, Ill.). One month old Balb/c mice (10 mice per peptide) are bled through the tail vein on day one and immunized intraperitoneally using 20–100 µg KLH-peptide complex (day one, in complete Freund's adjuvant (Pierce Chemical Co., Rockford, Ill.); day 14, in incomplete Freund's adjuvant (Pierce Chemical Co. Rockford, Ill.); day 28, in incomplete Freund's adjuvant). On day 35, the injection is given intravenously without adjuvant. If only BSA-peptide complex is soluble, it is injected instead of the KLH-peptide complex. On day 38, the mice are sacrificed by cervical dislocation, the splenocytes removed, washed in cold Dulbecco's MEM (DMEM) without serum and fused with mouse myeloma X-63 Ag 8.563 at 37° C. for 1.5 minutes using polyethylene glycol (PEG), molecular weight 1,500 (Merck, N.J.).

After washing out the PEG three times in DMEM with 10% bovine serum, cells are seeded in DMEM with 20% fetal bovine serum and HAT supplement on 96 well plates with preseeded feeder splenocytes from normal mice (one normal feeder spleen for 4 plates, and one immune spleen for 6 plates). The cultures are left for 7–10 days. Culture medium is changed once a week until clonal growth is observed. Positive hybridoma clones are assayed by indirect immunofluorescence on HCC tissue sections and/or ELISA and propagated until enough antibody is collected. Positive hybridomas are frozen during subculture on a weekly basis.

Although the invention has been described with reference to presently preferred embodiments, it should be understood that various modifications can be made without departing from the spirit of the invention.

That which is claimed is:

1. A probe, comprising an oligonucleotide, which hybridizes under conditions comprising 0.2M sodium phosphate (pH 7.2), 50% formamide and 7% sodium dodecyl sulfate and a temperature of 64° C. to a nucleic acid selected from the group consisting of polynucleotides encoding SEQ. ID No: 2 and polynucleotides complementary to those encoding SEQ ID NO: 2.

2. The probe of claim 1, wherein the oligonucleotide consists of at least 40 contiguous nucleic acid residues.

3. The probe of claim 2, wherein the oligonucleotide consists of at least 60 contiguous nucleic acid residues.

4. The probe of claim 3, wherein the oligonucleotide consists of at least 150 contiguous nucleic acid residues.

5. The probe of claim 1, which is RNA.

6. The probe of claim 1, which is DNA.

7. The probe of claim 1, which is labeled.

8. The probe of claim 7, wherein the label is selected from the group consisting of radiolabels and fluorescent labels.

9. The probe of claim 8, wherein the radiolabel is selected from the group consisting of $^{32}P$, $^{14}C$, $^{125}I$, $^{3}H$, and $^{35}S$.

10. The probe of claim 8, wherein the label is a fluorescent label.

11. The probe of claim 7, wherein the label comprises a protein.

12. The probe of claim 11, selected from the group consisting of biotin and biotin analogue labeled probes.

13. The probe of claim 11, wherein the protein is radiolabeled or fluorescently labeled.

14. The probe of claim 11, wherein the protein comprises a single-stranded histone binding protein.

15. The probe of claim 1, wherein the polynucleotide comprises nucleotides 24–132 of SEQ. ID No: 1.

16. The probe of claim 1, wherein the oligonucleotide is complementary to the nucleic acid.

17. The probe of claim 1, wherein the oligonucleotide hybridizes to a nucleic acid encoding SEQ. ID No: 2.

18. The probe of claim 17, wherein the oligonucleotide is complementary to the nucleic acid.

19. The probe of claim 17, wherein the oligonucleotide hybridizes to a nucleic acid comprising SEQ. ID No: 1.

20. The probe of claim 19, wherein the oligonucleotide is complementary to the nucleic acid.

21. The probe of claim 1, wherein the oligonucleotide hybridizes to a nucleic acid complementary to those encoding SEQ. ID No: 2.

22. The probe of claim 21, wherein the oligonucleotide is complementary to the nucleic acid.

23. The probe of claim 21, wherein the oligonucleotide hybridizes to a polynucleotide complementary to SEQ. ID No: 1.

24. The probe of claim 23, wherein the oligonucleotide is complementary to the nucleic acid.

25. A composition, comprising the probe of claim 1 and a carrier.

26. A method of detecting the presence of a nucleic acid associated with neoplastic liver disease, comprising contacting nucleic acids present in a biological sample with the probe of claim 1, under conditions effective to hybridize the probe to the nucleic acid encoding a protein associated with neoplastic liver disease or fragments thereof;

allowing the formation of double stranded hybrids between the probe and any hybridizing nucleic acid, or fragments thereof present in the sample; and detecting the presence of the resulting double stranded hybrids.

27. The method of claim 26, wherein the probe is detectably labeled.

28. The method of claim 27, wherein the nucleic acid present in the sample is DNA.

29. The method of claim 26, wherein the nucleic acid present in the sample is RNA.

30. The method of claim 26, wherein the neoplastic liver disease is selected from the group consisting of liver cirrhosis and hepatocellular carcinoma.

31. The method of claim 26, wherein the hybridization is conducted under conditions comprising 0.2M sodium phosphate (pH 7.2), 50% formamide and 7% sodium dodecyl sulfate and a temperature of 64° C.

32. The method of claim 26, wherein the nucleic acid present in the sample is separated from other cell components by lysis.

33. The method of claim 26, wherein the sample is a tissue sample.

34. A method of diagnosing a neoplastic liver disease, comprising contacting nucleic acids present in a biological sample with the probe of claim 1, under conditions effective to hybridize the probe to the nucleic acid encoding a protein associated with neoplastic liver disease, or fragments thereof;

allowing the formation of double stranded hybrids between the probe and any hybridizing nucleic acid, or fragments thereof present in the sample; and detecting the presence of the resulting double stranded hybrids.

35. The method of claim 34, wherein the probe is detectably labeled.

36. The method of claim 34, wherein the nucleic acid present in the sample is DNA.

37. The method of claim 34, wherein the nucleic acid present in the sample is RNA.

38. The method of claim 34, wherein the neoplastic liver disease is selected from the group consisting of liver cirrhosis and hepatocellular carcinoma.

39. The method of claim 34, wherein the hybridization is conducted under conditions comprising 0.2M sodium phosphate (pH 7.2), 50% formamide and 7% sodium dodecyl sulfate and a temperature of 64° C.

40. The method of claim 34, wherein the nucleic acid present in the sample is separated from other cell components by lysis.

41. The method of claim 24, wherein the sample is a tissue sample.

42. A nucleic acid construct, comprising the probe of claim 1;

an origin of replication; and a promoter.

43. A vector, comprising the probe of claim 1.

44. The vector of claim 43, which is an expression vector.

45. A composition, comprising the vector of claim 43; and a carrier.

46. A host cell, transfected with the probe of claim 1.

47. A host cell, transfected with the nucleic acid construct of claim 42.

48. A host cell, transfected with the vector of claim 43.

49. A method of amplifying a probe, comprising culturing the host cell of claim 47 in a growth medium and under amplifying conditions; and allowing the construct to accumulate.

50. The method of claim 49, further comprising separating the construct from the medium and the cells.

51. The method of claim 49, further comprising cleaving the nucleic acid construct and separating the probe from the cleaved nucleic acid construct.

52. A neoplastic liver diagnostic kit, comprising the probe of claim 1; and instructions for its use.

53. The kit of claim 52, wherein the probe is provided as nucleic acid construct which further comprises an origin of replication and a promoter.

54. The kit of claim 53, wherein the construct is provided as a host cell transfected with the construct.

55. The kit of claim 52, wherein the probe is linked to a vector.

* * * * *

UNITED STATES PATENT AND TRADEMARK OFFICE
CERTIFICATE OF CORRECTION

PATENT NO.     : 5,866,329                                        Page 1 of 1
DATED          : February 2, 1999
INVENTOR(S)    : Achilles A. Demetriou and Julia Y. Ljubimova It is certified that error appears in the above-identified patent and that said Letters Patent is hereby corrected as shown below:

<u>Column 18,</u>
Line 38, after "liver" and before "diagnostic kit," please insert -- disease --.

Signed and Sealed this

Third Day of June, 2003

JAMES E. ROGAN
*Director of the United States Patent and Trademark Office*